US009302090B2

(12) United States Patent
Williams et al.

(10) Patent No.: US 9,302,090 B2
(45) Date of Patent: Apr. 5, 2016

(54) PHOTOLUMINESCENT COUPLING

(75) Inventors: Derek M. Williams, Cuyahoga Falls, OH (US); Grant W. Phillips, Richfield, OH (US); George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 900 days.

(21) Appl. No.: 13/557,850

(22) Filed: Jul. 25, 2012

(65) Prior Publication Data
US 2014/0031754 A1    Jan. 30, 2014

(51) Int. Cl.
*A61M 39/20* (2006.01)
*A61M 39/10* (2006.01)

(52) U.S. Cl.
CPC .......... *A61M 39/20* (2013.01); *A61M 39/1011* (2013.01); *A61M 2039/1027* (2013.01); *A61M 2039/1044* (2013.01); *A61M 2039/1083* (2013.01)

(58) Field of Classification Search
CPC .......... A61M 39/26; A61M 2205/583; A61M 2039/1044; A61M 2205/6063; A61B 2019/5441
See application file for complete search history.

(56) References Cited

U.S. PATENT DOCUMENTS

| 4,863,438 A | 9/1989 | Gauderer et al. |
| 5,007,900 A | 4/1991 | Picha et al. |
| 5,008,551 A * | 4/1991 | Randolph ................. 250/462.1 |
| 5,458,583 A * | 10/1995 | McNeely et al. ........ 604/103.13 |
| 5,685,866 A * | 11/1997 | Lopez .......................... 604/249 |
| 5,690,612 A | 11/1997 | Lopez et al. |
| 5,695,466 A | 12/1997 | Lopez et al. |
| 6,019,746 A | 2/2000 | Picha et al. |
| 6,022,500 A | 2/2000 | John et al. |
| 6,142,446 A | 11/2000 | Leinsing |
| 6,364,858 B1 | 4/2002 | Picha |
| 6,997,909 B2 * | 2/2006 | Goldberg ...................... 604/175 |
| 7,115,297 B2 | 10/2006 | Stillman |
| 7,184,825 B2 | 2/2007 | Leinsing et al. |
| 7,244,249 B2 | 7/2007 | Leinsing et al. |
| 7,306,199 B2 | 12/2007 | Leinsing et al. |
| 7,374,318 B2 | 5/2008 | Brooks et al. |
| 7,497,848 B2 | 3/2009 | Leinsing et al. |
| 7,527,123 B2 | 5/2009 | Puder |

(Continued)

FOREIGN PATENT DOCUMENTS

WO          95/03509 A2    2/1995

OTHER PUBLICATIONS

G-JET™ Low Profile Gastric-Jejunal Enteral Tube, <http://www.amtinnovation.com/button_G-JET.html>, date printed Jul. 25, 2012.

(Continued)

*Primary Examiner* — Aarti B Berdichevsky
(74) *Attorney, Agent, or Firm* — Pearne & Gordon LLP

(57) ABSTRACT

A coupling includes a first input port and a photoluminescent portion associated with the first input port. The first input port may be one or more of a gastric port, a jejunal port, or a balloon port. The first port may have a first glow-in-the dark feature and a second port may have a second glow-in-the-dark feature, which may be different from one another. The coupling may include means for orientation that assists a user in properly orienting a connector to be mounted in the first port in proper orientation and a first connector for coupling to the first port.

7 Claims, 5 Drawing Sheets

(56) References Cited

U.S. PATENT DOCUMENTS

| | | |
|---|---|---|
| 8,048,056 B2 | 11/2011 | Picha et al. |
| 2003/0225369 A1 | 12/2003 | McMichael et al. |
| 2004/0024363 A1* | 2/2004 | Goldberg ................. 604/175 |
| 2006/0260865 A1 | 11/2006 | Puder |
| 2008/0082051 A1 | 4/2008 | Miller et al. |
| 2008/0110456 A1 | 5/2008 | Flynn et al. |
| 2009/0156953 A1 | 6/2009 | Wondka et al. |
| 2009/0259097 A1 | 10/2009 | Thompson |
| 2010/0010339 A1 | 1/2010 | Smith et al. |
| 2010/0132237 A1 | 6/2010 | McDermott et al. |
| 2013/0298434 A1* | 11/2013 | McDermott et al. ............ 40/633 |
| 2014/0194823 A1* | 7/2014 | Phillips et al. ................ 604/175 |

OTHER PUBLICATIONS

International Search Report of International Application No. PCT/US2013/051924; dated Dec. 12, 2013.

* cited by examiner

PHOTOLUMINESCENT COUPLING

FIELD

The technology described herein relates to a photoluminescent, or glow-in-the-dark, coupling. In particular, the technology described herein may be used in connection with enteral feeding.

BACKGROUND

There have been many advancements in the field of gastric feeding devices, such as gastric button devices. Original devices had only one port that provided direct access to a patient's stomach for food and medication administration. With a single port, the use of the device was somewhat simple and straightforward. Newer devices provide two and three ports. For example, newer gastric feeding buttons have a balloon that allows the device to be maintained in the stomach of a user. A port, which is positioned next to the gastric feeding port, is used for introducing water, or in some cases air, into the balloon. More advanced feeding devices, known as Gastric-Jejunal Buttons or (G-J Buttons) have a third port that is used for jejunal feeding. The addition of additional ports provides a greater potential for user error.

Manufacturers have taken steps to design unique characteristics that are used to distinguish the three ports, including dimensional differences, incompatible connections, color differences, printed labels, and indicators molded directly into the devices themselves. Despite all of these steps to ensure that the feeding button is used properly by the end-user, there remains a risk of an accidental connection to an incorrect port. Due to the types of patients that necessitate these particular medical devices, administering food intended for the jejunal port into the gastric port could lead to vomiting and aspiration of stomach contents—a potentially dangerous situation. Thus, care must be taken by the end user to avoid accidental device misuse.

One target patient population for gastric feeding devices is pediatric patients with poor gastric motility. Since these patients will receive most of their nutrition through the jejunal-access port, they will be connected to a feeding pump most of the day and night. Consequently, the patient's caregivers may have to connect and disconnect adapters to the jejunal-access port at night while the patient is asleep. This gives the caregivers two options—they can either turn on a light in order to visually see the device and its different ports, or they can keep the lights off (trying not to disturb the child's sleep) and attempt to make any necessary adjustments to the device by memory and "feel."

The first option of turning on the light presents a risk of waking the child, who is already in compromised health. The second option deprives the caregiver of the benefits of many of the unique characteristics that are used to distinguish between the three access ports, as described above, and, thus, presents a risk of accidental connection or administration errors.

SUMMARY

In accordance with the teachings described herein, a coupling for administering food or medication to a patient is described.

BRIEF DESCRIPTION OF THE DRAWING FIGURES

FIG. 8 is a cross-sectional view of an example glow-in-the-dark feature applied to a port, where the glow-in-the-dark feature is molded in;

DETAILED DESCRIPTION

Figure 1:
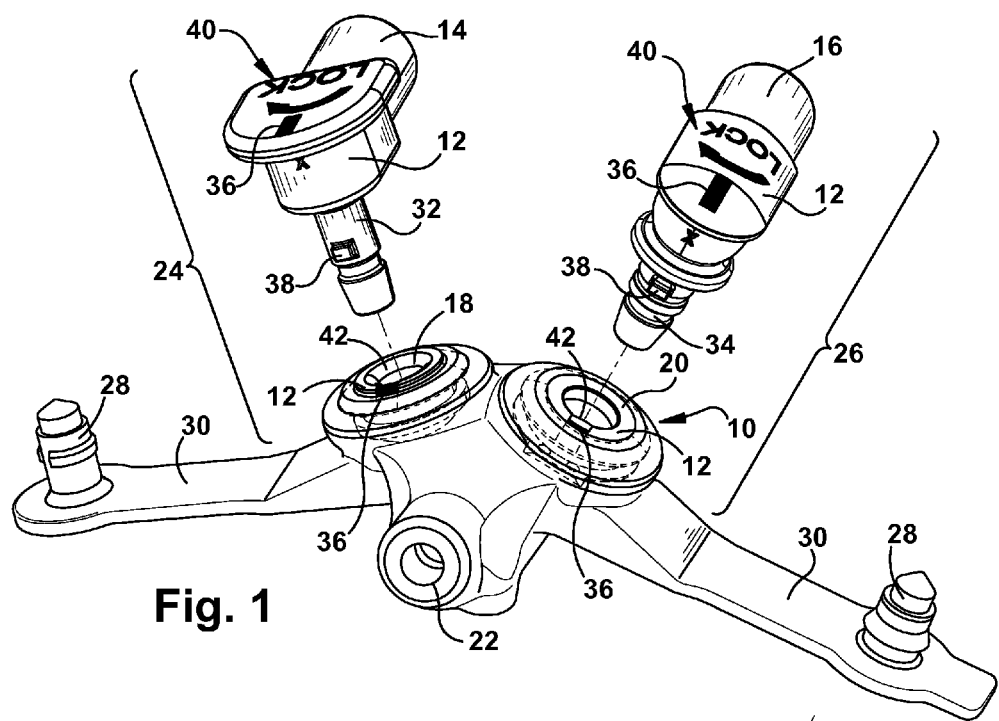
FIG. 1 is a perspective view of an enteral feeding tube having a first port, a second port, and a third port.

The technology described herein relates generally to a coupling 10 that has an example glow-in-the-dark or photoluminescent feature 12 that is used to help a user to locate and/or properly orient an adapter or connector 14, 16 with an input port 18, 20 in a dark environment. The example portions of the coupling 10 are generally made of plastic and allow the part to glow-in-the-dark when ambient light is too low to visualize the coupling 10 properly. It is desirable to be able to avoid turning on the lights when a child is sleeping. Thus, the example glow-in-the-dark feature 12 allows a caregiver to access the coupling 10 without turning on the lights. It should be noted that when the term glow-in-the-dark is utilized, it is also meant to encompass photoluminescent and other glow-in-the-dark materials. In addition, when the term photoluminescent is used, it is meant to encompass any number of glow-in-the-dark materials. The terms should be considered to be interchangeable when used herein. In addition, the terms adapter and connector 14, 16 should be considered to be interchangeable when used herein, but can refer to any type of device that may be associated with an opening, a port, or a coupling.

The coupling 10 with the example glow-in-the-dark features 12 may include a glow-in-the dark input port 18, 20, 22 and a glow-in-the-dark connector 14, 16 for coupling with the port 18, 20, such as a feeding tubes 24, 26. Other types of devices may also be useful with the examples described herein, including those not limited to enteral use, such as those relating to parenteral and other uses, as will be discussed in greater detail below.

In one example, a coupling 10 includes an input port 18, 20 and a connector 14, 16 for coupling with the input port 18, 20. The input port 18, 20 includes at least a portion that glows-in-the-dark 12. The connector 14, 16 may also include a glow-in-the-dark portion 12 that is meant to couple with the glow-in-the-dark input port 18, 20. The input port 18, 20 and connector 14, 16 glow-in-the-dark portions 12 may be made of the same glow-in-the-dark resins, if desired, or of different glow-in-the-dark resins.

The glow-in-the-dark resins that are used with the example couplings 10 need minimal light exposure to charge because, in general, the couplings 10 will only have limited exposure times to ambient light. Glow-in-the-dark plastic resins should emit enough light to help the caregiver ensure proper coupling of the connector 14, 16 to the input port 18, 20 during low-light conditions. The glow-in-the-dark plastic resins should emit enough light throughout the night without necessitating a "re-charge" and should be biocompatible.

By providing a glow-in-the-dark material 12 that has the above-describe properties, caregivers (either healthcare professionals or parents) may confidently access different ports 18, 20, 22 within a feeding tube 24, 26 in low-level light conditions. Furthermore, as will be discussed below, the example couplings 10 help to prevent dangerous incorrect connections while giving the patient a better chance to sleep through the night uninterrupted.

The types of materials that may be used for the example glow-in-the-dark features 12 are non-limiting, as long as they charge upon exposure to ambient light and they remain charged for an extended period of time, such as 4, 6, 8 or 12 hours. Different glow colors and glow strength may be desirable under certain circumstances. Thus, different types of glow-in-the-dark materials may be useful instead of the use of a single glow in the dark material. Materials that charge quickly are useful, although those that don't charge quickly may also be useful. The expense of the material along with the particular strengths of the material, such as color, glow strength, length to charge, length to remain changed, etc., should be considered when selecting a glow-in-the-dark material. Any number of other materials may be used, as known by those of skill in the art, as well as materials that may be developed in the future.

Referring now to the figures, FIGS. 1-4 show an example coupling 10 that is utilized as a button for a G-J tube. This device 10 has an input port 18 for gastric input, an input port 20 for jejunal input, and an input port 22 for filling a balloon with a liquid. The gastric port 18 faces upwardly and is shown on the left side of the button 10. The jejunal port 20 faces upwardly and is shown on the right side of the button 10. The input port 22 for the balloon is positioned on the side of the device 10 and is shown facing forwardly. Both the gastric and jejunal input ports 18, 20 have a plug 28 that is attached to the button 10 with a strip of plastic material 30, so that when the ports 18, 20 are not coupled to a connector 14, 16, they can be closed by the plug 28. The balloon input port 22 is self-closing. A full description of a G-J button 10 similar to that shown in the examples may be found at www.amtinnovation.com/button_G-JET.html. Similar devices are also discussed in U.S. Pat. Nos. 4,863,438, 5,007,900, 6,019,746, 6,364,858, and 8,048,056.

In the case of the G-J tube, one troubling type of misconnection involves administering feeding intended for the jejunal-access port 20 into the gastric-access port 18. One way to deter this type of mishap under low-light conditions is to only make the jejunal-access port 20 and the jejunal feeding tube coupling adapter 16 glow-in-the-dark. This way the caregiver would be forced to focus on the access port 20 that is glowing-in-the-dark, helping to lessen the possibility of connecting to the incorrect port (which would not be glowing). An example of this is shown in FIGS. 1 and 2.

Another possibility for the G-J tube would be to use two totally different glow-in-the-dark colors for the gastric-access port 18 and the jejunal-access port 20 and connectors 14, 16. If the gastric-access port 18 and its matching adapter 14 was glow-in-the-dark green, for example, while the jejunal-access port 20 and its matching adapter 16 was glow-in-the-dark orange, for example, the caregiver would be able to distinguish both ports 18, 20 in low-level light conditions. Glowing strength or intensity may also be adjusted such that the primary jejunal port 20 glows much brighter than the secondary gastric port 18. Thus, a caregiver could distinguish between the connectors 14, 16 to associate them with the proper port 18, 20.

Importantly, different types of feeding compounds are administered for jejunal feeding as compared to gastric feeding. Thus, it is important that a user does not accidentally administer gastric feeding matter to the jejunal port 20 and vice versa. Such accidental feeding can result in harm to a patient. Thus, it is important to properly label and/or identify the ports 18, 20 so that a user can easily determine which port is used for jejunal feeding and which port is used for gastric feeding.

Figure 2:
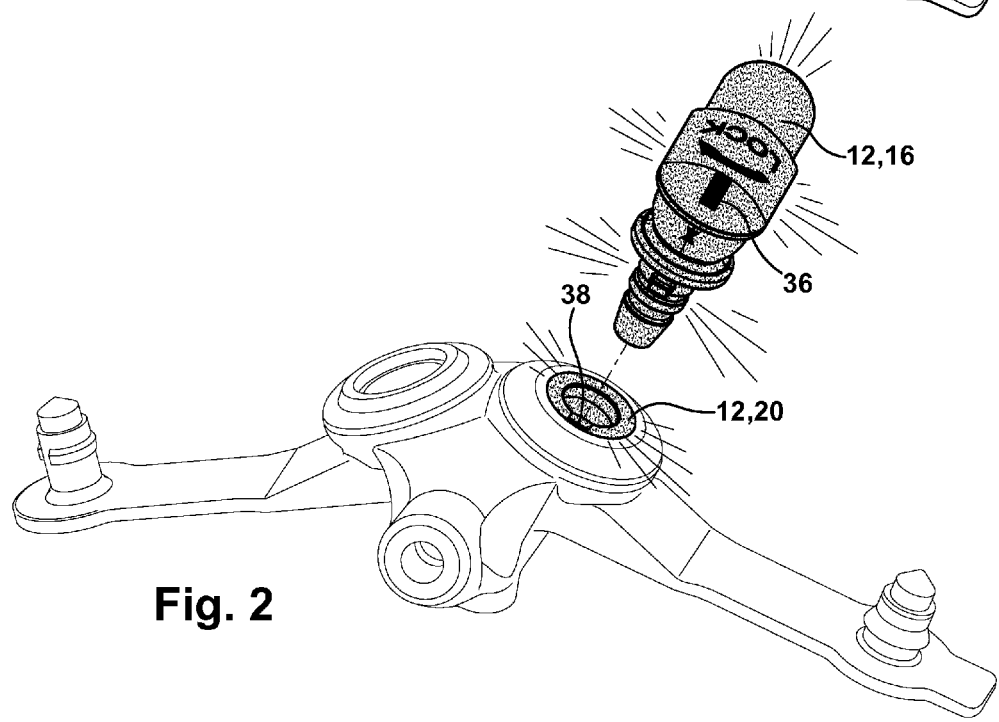
FIG. 2 is a perspective view of the enteral feeding tube of FIG. 1 in a darkened state, showing how one of the ports has an example glow-in-the-dark feature and one of the adapters has a glow-in-the-dark feature.
Figure 3:
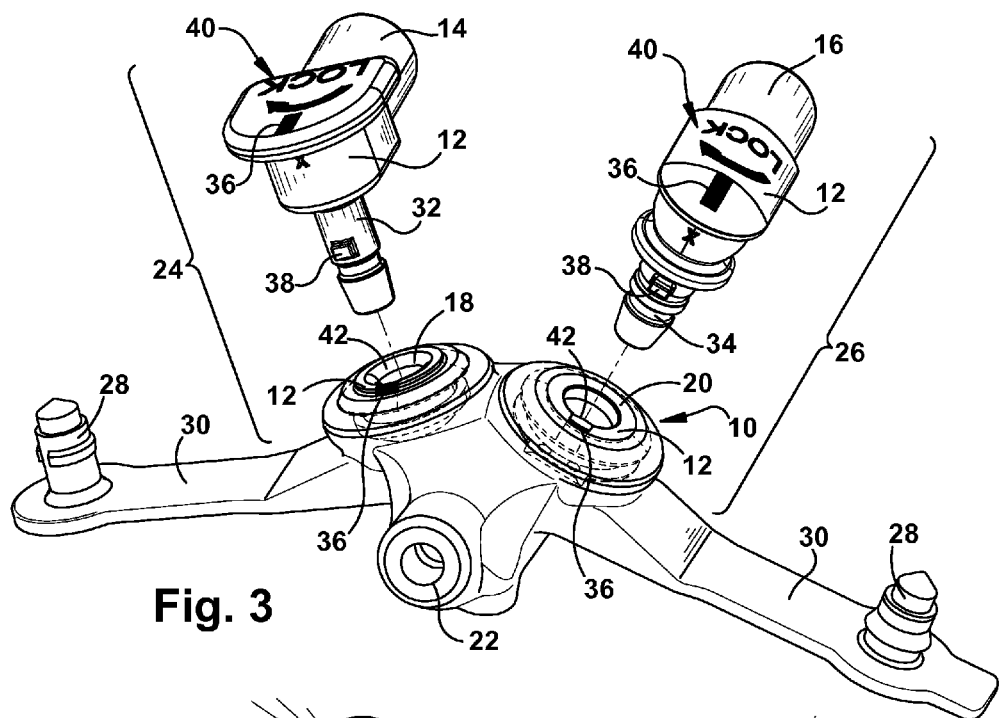
FIG. 3 is a perspective view of an enteral feeding tube similar to that shown in FIG. 1, but where both the first and second ports have the example glow-in-the-dark feature.

As shown in FIGS. 1 and 3, the jejunal port 20 is positioned on the right side of the coupling 10 and the gastric port 18 is positioned on the left side of the coupling 10. The feeding tube connector 16 that is associated with the jejunal port 20 has a shape that is different from the feeding tube connector 14 that is associated with the gastric port 18. As shown, the head 32 of the connector is smaller for the gastric connector 14 than is the head 34 of the jejunal connector 16. Different shapes may be used as a means for distinguishing the part and/or connectors. The connectors 14, 16 can also be made in different colors or labeled appropriately, if desired. Thus, a caregiver who is familiar with the connectors 14, 16 and their shape can readily determine which connector 14, 16 should be used for jejunal feeding and which connector should be used for gastric feeding.

However, in low light conditions, such as in a bedroom of a patient at night, a caregiver may have difficulty in determining which connector 14, 16 should be used with which port 18, 20. The present example port 18, 20, 22 and connector 14, 16 helps to remedy any difficulty that a caregiver may experience by providing a portion of the input port 18, 20, 22 with a glow-in-the-dark portion 12. As shown in FIGS. 1 and 2, the jejunal port 16 glows in the dark and is formed as an insert that is positioned in the port in order to highlight the port 16. Alternatively, the glow-in-the-dark portion may be coupled to the port in any known manner.

The port 16 alone may be glow-in-the-dark, or the connector 20 may also glow in the dark. In the example of FIG. 2, both the input port 20 and the connector 16 glow-in-the-dark. The port 20 and connector 16 may be the same color. Although helpful to a user, this is not required. The connector 16 may also have labeling provided on a surface of the connector 16 or input port 20. In the example shown, the connector 16 and input port 20 glow-in-the-dark and both have black lines 36 that identify an alignment mark 36 for aligning the connector 16 with a key shape 38 to an input port 20, as well as labeling 40 to assist the user in locking the connector 16 into the port 20. Other labeling could also be used that assists the user in identifying the type of port.

In addition, as shown in FIG. 2, the blackened line 36 of the input port 20 identifies a location for a shape change 42 in the port 20. In the example shown, the port 20 has a key-hole shape 42 for accepting a key or protrusion 38 that is positioned on the connector 16. The key 38 seats within the notch 42 of the input port 20 and allows the connector 16 to be fully inserted into the port 20. Then the connector 16 can be locked in place by rotating the connector head 34 into a locked position such that the key 38 is positioned under a portion 44 of the input port 20. The blackened line 36 on the input port 20 can be created in any known fashion, such as by printing black pad ink over or into the photoluminescent material, or by leaving a break 46 (shown in FIG. 10) in the photoluminescent material, among other known techniques.

Figure 4:
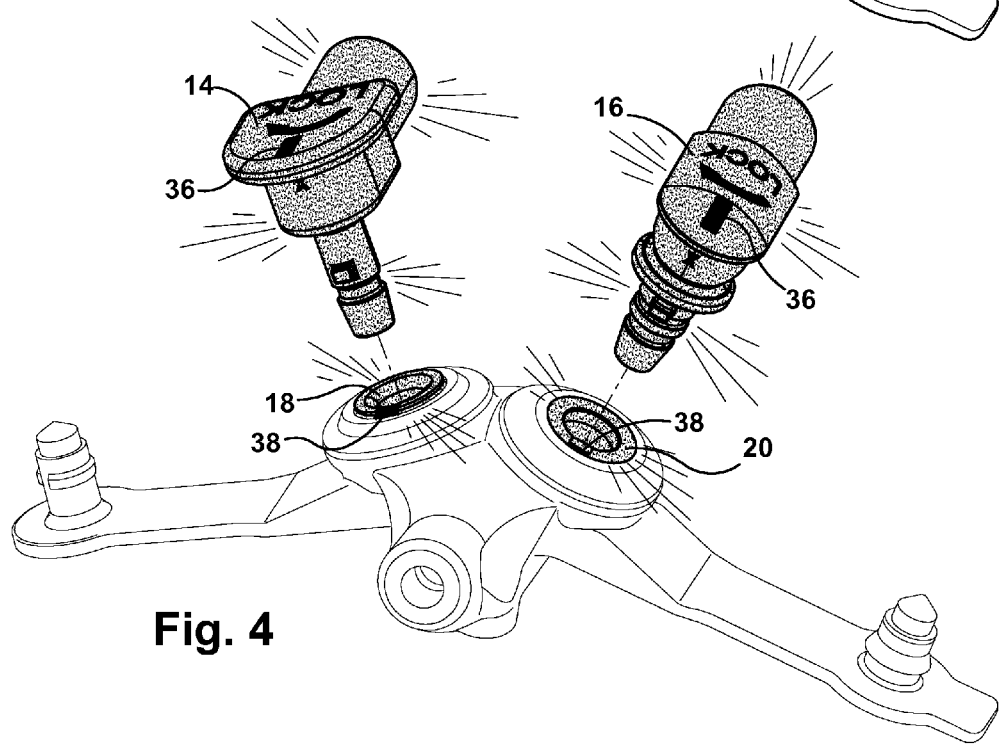
FIG. 4 is a perspective view of the enteral feeding tube of FIG. 3 in a darkened state, showing how two of the ports have an example glow-in-the-dark feature and both adapters have glow-in-the-dark features.

FIGS. 3 and 4 concern a device similar to that shown in FIGS. 1 and 2, but in this example, both the gastric and jejunal input ports 18, 20 have a photoluminescent portion 12 and both connectors 14, 16 are photoluminescent 12. While the entire body of the connector is shown as being photoluminescent, portions of the body (not shown) or labeling on the body of the connectors 14, 16 could alternatively be photoluminescent. In FIG. 4, the gastric connector 14 and port 18 both glow in the same color, such as green, while the jejunal input port 20 and connector 16 both glow in the same color that is different from the color of the gastric feeding tube 24, such as orange. Alternatively, the two ports 18, 20 and/or connectors 14, 16 could glow in the same color, but with different intensities, or the two ports 18, 20 and/or connectors 14, 16 could glow in the same color, but have different labeling that is visible in a darkened environment. One or the other of the ports and connectors could be glow-in-the-dark portions.

As with the example shown in FIGS. 1 and 2, the input ports 18, 20 have a key hole 42 or notched shape for accepting a key or protrusion 38 that is positioned on the respective connector 14, 16. Each connector 14, 16 may have an alignment label 32 and each input port 18, 20 may have an alignment feature, such as a blackened line 32, to indicate the orientation of the connector 14, 16 for proper insertion into the input port 18, 20.

Figure 5:
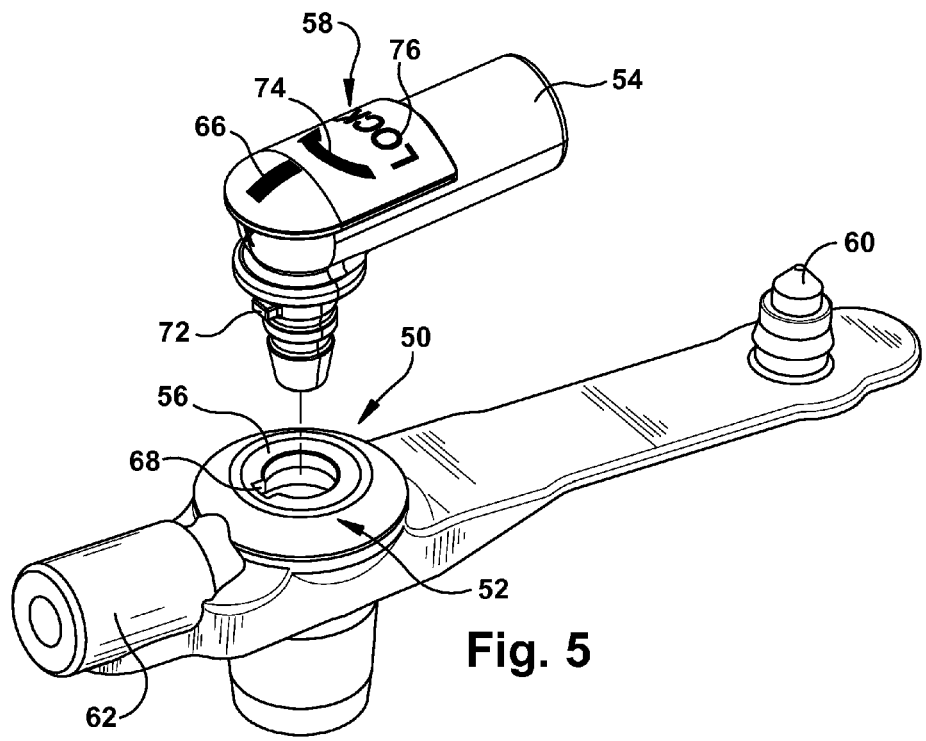
FIG. 5 is a perspective view of a different enteral feeding tube having a first port for feeding and a second port for a balloon.
Figure 6:
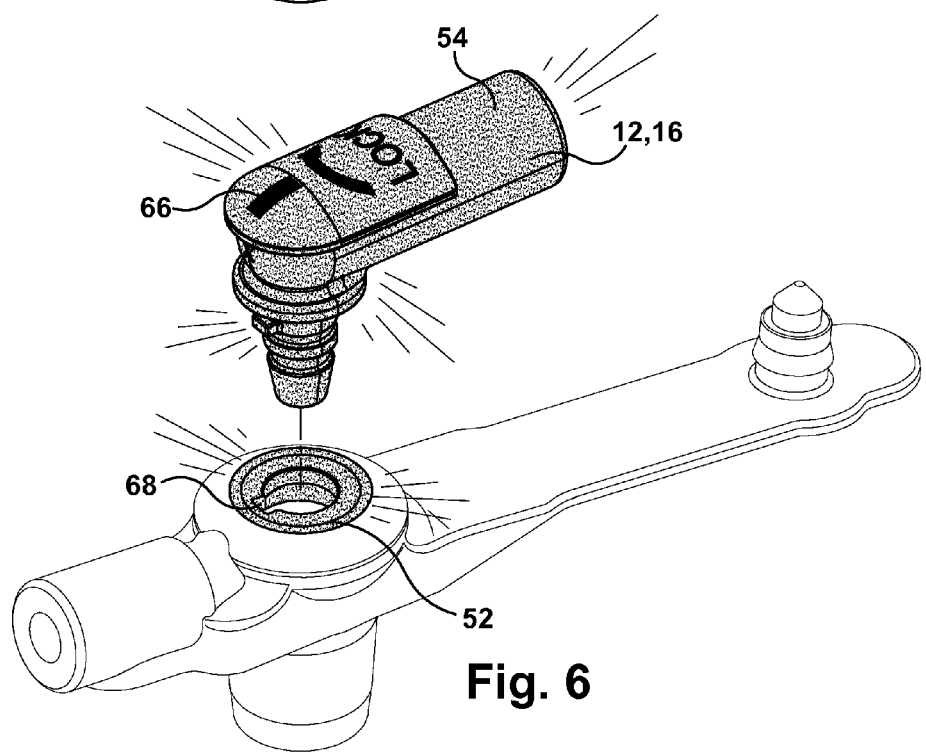
FIG. 6 is a perspective view of the enteral feeding tube of FIG. 5 in a darkened state, showing how one of the ports has an example glow-in-the-dark feature and an adapter has a glow-in-the-dark feature.

FIGS. 5 and 6 depict a different type of coupling device 50 that has a single input port 52 for food delivery and a balloon access port 62 for filling a balloon in order to maintain the device in position on the body of a patient. Even though the possibility of mixing up the balloon-access port 62 and the feeding-access port 52 is rare, a glow-in-the-dark feeding-access port 52 and connector 54 would assist caregivers during connections and disconnections at night. This would lessen the likelihood of interrupting the sleep of the patient.

In the device 50, shown in FIGS. 5 and 6, the input port 52 for food delivery faces upwardly and is associated with a connector 54. One type of device 50 of this nature that is presently known is the AMT Mini One® Gastrostomy Button 50. In the device shown, the input port 52 has a ring 56 of photoluminescent material that is used to locate the input port 52 in a dark setting. The ring may be coupled with or formed into the button 50 in any known manner.

In addition, the connector 54 may also be made of a photoluminescent material 12 that matches the photoluminescent material 12 of the input port ring 56. Alternatively, the connector 54 may be non-photoluminescent or the connector 54 may be a different color or glow intensity from the photoluminescent material of the input port 52. The input port 52 may have a shape that is conducive to a single orientation for the connector 54, or that only allows one size of connector 54 to be inserted into the port 52. This may assist in preventing accidental connection of the wrong connector. In addition, the connector 54 and/or input port 52 may have labels, such as markings, symbols, or wording, that are used to assist a user in properly orienting the connector 54 relative to the input port 52. In addition, labels 58 may be used to properly identify the port 52 and/or connector 54.

The device shown in FIG. 5 also includes a plug 60 that is connected to the coupling 10 for plugging the input port 52 when the connector 54 is not inserted into the input port 52. In addition, the input port 62 for the balloon is shown extending to the side relative to the coupling 50. The balloon input port 62 shown does not have the same shape or size as the input port 52 for food delivery, making it harder to accidentally administer food through the balloon port 62. In addition, the balloon port 62 shown is self-closing and does not require a plug. Alternatively, a plug could be used if desired or needed.

Figure 7:
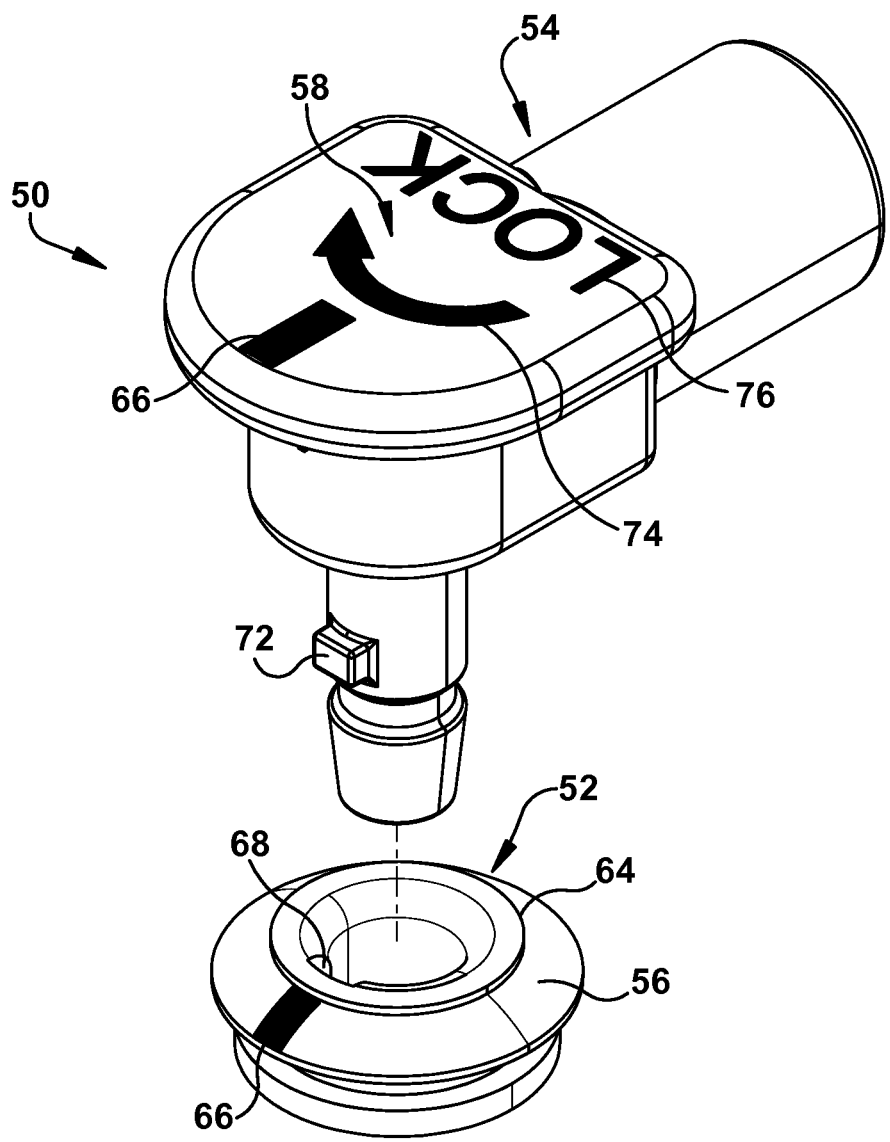
FIG. 7 is an exploded view of the example glow-in-the-dark features of the feeding tube shown in FIGS. 1-4.

FIG. 7 depicts an exploded view of an input port ring 56 that is coupled to or molded into the coupling 50, as well as a connector 54 for use with the input port ring 56. The input port ring 56 and connector 54 may both be photoluminescent 12. The ring 56 has a lip 64 around a top edge for seating under part of the coupling 50 during the molding process. The ring 56 also has a strip of black ink 66 and a notch 68 that are together used for aligning a connector 54 with the port 52. The strip of black ink 66 is aligned with the notch 68 and is utilized to assist a user in locating the notch 68 for proper orientation of a connector 54. The general shape of the input port 52 is round, except for the notch 68. The black line 66 may be positioned under a clear portion of the coupling 50 so that it is visible when the input port 52 is molded into the coupling 10. The coupling 50 may be made of a transparent material, or of another material if desired. In the event that the coupling 50 is not made of a transparent material, the input port 52 can be formed so that the black line marking 66 is visible. Alternatively, the black line marking 66 can be positioned in a different location, such as on the notch 68 itself, or a different marking can be used.

Figure 10:
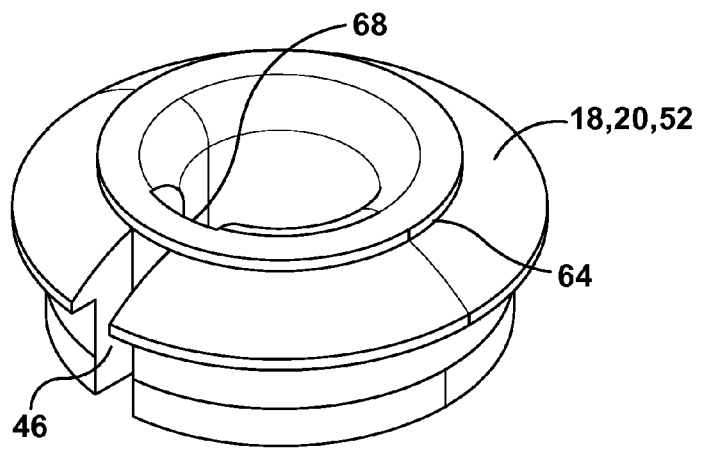
FIG. 10 is a top view of an input port with photoluminescent material that has a break in the material.

Instead of a black ink line 66 that is printed or otherwise disposed on the surface of the input port 52, a break 46 in the photoluminescent material 12 of the input port 52 may be used to provide a line for orientation purposes, such as shown in FIG. 10. Other types of markings may alternatively be used, including non-printed markings, stickers and the like.

As shown in FIG. 7, the connector 54 has a key 72 for seating in the input port 52. The key 72 that is used to align the connector 54 with the input port 52 has a shape that allows it to fit within the notch 68. In addition, the connector 54 also has a line printed 66 or otherwise disposed on the surface of the connector 54 for aligning with the notch 68 and which serves as an orientation indicator. The connector 54 also has an arrow 74 and the word "lock" 76 disposed on an upper surface thereof for indicating how the connector 54 may be locked into the input port 52.

The input port 52 may have disposed on a lower surface thereof a ledge 78 that is positioned directly adjacent the notch 68. The ledge 78 is designed to hold the key 72 under the ledge 78 in order to hold the connector 54 in the input port 52. Other types of connection mechanisms may alternatively be utilized. The ledge 78 can be positioned on part of the coupling 50 instead of or in addition to being positioned on the input port ring 52. The connector 54 is designed to prevent leakage from the input port 52 when properly connected. Other indicia or markings may be provided on the connector 54 or on the input port 52 or coupling 50 in order to assist a user in locking, aligning, or otherwise using the connector 54 and input port 52.

Figure 8:
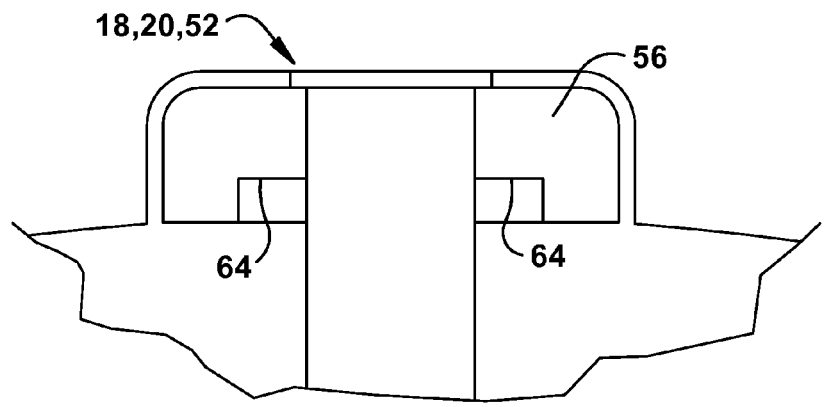
Figure 9:
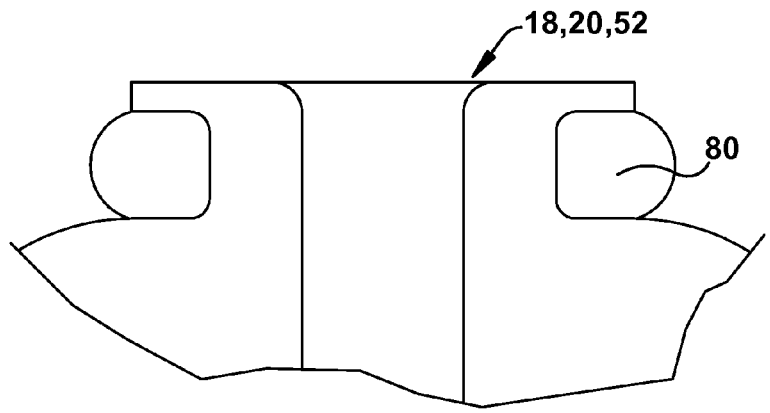
FIG. 9 is a cross-sectional view of an example glow-in-the-dark feature applied to a port, where the glow-in-the-dark feature is externally applied.

FIGS. 8 and 9 show different types of manufacturing methods for incorporating a photoluminescent material 12 into a coupling 10, 50. FIG. 8 depicts an example of a ring 56 that is molded into the port and FIG. 9 depicts an example of an externally applied ring 80. Other types of manufacturing methods and/or designs may alternatively be used. For example, a sticker could be applied to an exterior surface of the coupling 10, 50, or a photoluminescent material could be applied to an exterior surface of the coupling 10, 50. Instead of having the entire connector 14, 16, 54 be made of a photoluminescent material, portions of the connector could be photoluminescent (not shown), or portions of the connector could have photoluminescent materials applied thereto (not shown) in any known manner, such as via printing, sticker, or other means of application.

The glow-in-the-dark principles discussed herein may also be applied to other medical devices that require connections and disconnections in low-level light conditions. Nightly rounds are a common practice in hospitals, and patients are often woken up simply because the lights need to be turned on to make adjustments to devices and couplings. Glow-in-the-dark resins could be used in various couplings including intravenous and arterial lines, dialysis connections, Foley catheter connections, chest tubes, or any other type of liquid, gas, or vacuum connection used for patient care. The housings of the couplings can be color coded for different uses, and the dimensions of the glow-in-the-dark connectors can be varied to prevent misconnections. Glow-in-the-dark catheters and inter-lumen catheters can also be made using the above-described technology. This can help healthcare professionals visualize catheter placement in vessels near the surface of the patient's skin simply by turning the lights down low. If the glow-in-the-dark resins can be made to emit enough light, connectors can be made to help illuminate body cavities as well.

According to one example of the invention, an enteral coupling comprises a first input port and a photoluminescent portion associated with the first input port. The first input port is one or more of a gastric port, a jejunal port, or a balloon port. The first connector is for inserting into the first input port and may include a photoluminescent portion. The second input port may have a photoluminescent portion associated with the second input port and a second connector having a photoluminescent portion. The second connector is for inserting into the second input port. A third input port may also be provided with a third device for insertion into the third input port. The third input port and third device may or may not include a photoluminescent portion.

The photoluminescent portion of the first input port may be integrally coupled to the first input port or externally positioned on the first input port. A second photoluminescent portion having a color that is different from a color of the photoluminescent portion of the first input port may be utilized for indicating orientation. A break in the photoluminescent portion of the first input port for indicating orientation, wherein the break is provided by a second photoluminescent portion that has a different color from the photoluminescent portion of the first input port, or by a break in the material of the photoluminescent portion of the first input port, or by a darkened portion associated with the photoluminescent portion of the first input port.

The photoluminescent portion of the first input port may have a first color and the photoluminescent portion of the second input port may have a second color that is different from the first color. The photoluminescent portion of the first port may have a first color, the photoluminescent portion of the first connector may have a second color, the photoluminescent portion of the second input port may have a third color, and the photoluminescent portion of the second connector may have a fourth color. The first and second colors may be the same and the third and fourth colors may be the same. Alternatively, the first and second colors may be different from one another and the third and fourth colors may be different from one another.

The first input port may have an opening with a discontinuous portion for indicating orientation. The discontinuous portion may be provided by a notch, by black ink pad printing, by a break in the photoluminescent material of the first input port, by a blackened portion, or by a combination thereof.

In one example of the invention, the material of the photoluminescent portion of the first input port, second input port, first connector, or second connector charges with minimal light exposure and lasts for 8 or more hours. One or more of the photoluminescent portions may glow brighter than another of the photoluminescent portions.

The various parts of the coupling may include labels that are visible in the dark. The labels may be positioned on the photoluminescent portion of the first input port and may include black ink or another different photoluminescent portion.

The example coupling may include an orientation indicating means, wherein the orientation indicating means includes black ink, a different colored photoluminescent material, labeling, different shapes, darkened portions, or a combination thereof. Alternatively, the photoluminescent portion may be bright enough to illuminate a body cavity.

In another example of the invention, a coupling comprises a first port having a first glow-in-the dark feature and a second port having a second glow-in-the-dark feature. The first glow-in-the dark feature is different from the second glow-in-the-dark feature. The first glow-in-the dark feature may be a first glow-in-the dark color and the second glow-in-the dark feature may be a second glow-in-the dark color. Alternatively, or in addition thereto, the first glow-in-the dark feature may have a first glow-in-the dark intensity and the second glow-in-the dark feature may have a second glow-in-the dark intensity. Alternatively, or in addition thereto, the first glow-in-the dark feature may have a first glow-in-the dark shape and the second glow-in-the dark feature may have a second glow-in-the dark shape. Alternatively, or in addition thereto, the first glow-in-the dark feature may have a first glow-in-the dark labeling and the second glow-in-the dark feature may have a second glow-in-the dark labeling. A combination of any of the foregoing features may be utilized, as desired.

The coupling may be an enteral feeding tube. The coupling may also include a first connector for coupling with the first port and a second connector for coupling with the second port. The first connector may have a first glow-in-the-dark feature and the second connector may have a second glow-in-the-dark feature.

In another example of the invention, a coupling for administering food or medication comprises a first port having a glow-in-the-dark feature and means for orientation that assists a user in properly orienting a connector to be mounted in the first port in proper orientation, and a first connector coupled to the first port. The first connector is guided by the means for orientation in order to properly couple the first connector to the first port. The means for orientating may be one or more of a shape, a glow intensity, labeling, color, a break in the glow-in-the-dark features, texture, a darkened portion, or a combination thereof.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A gastric jejunal feeding device comprising:
   a gastric port;
   a jejunal port including a photoluminescent portion;
   a gastric connector, for coupling with the gastric port; and
   a jejunal connector, for coupling with the jejunal port, including a photoluminescent portion;
   wherein:
   the jejunal port has an opening with a notch for indicating orientation;
   the photoluminescent portion of the jejunal port includes a blackened portion for indicating orientation; and
   the jejunal connector includes a key for seating in the notch and allowing the jejunal connector to be fully inserted into the jejunal port.

2. The gastric jejunal feeding device of claim 1, wherein the blackened portion of the photoluminescent portion of the jejunal port comprises a line that identifies an alignment mark for aligning the jejunal connector including the key with the jejunal port.

3. The gastric jejunal feeding device of claim 1, further comprising a balloon port for filling a balloon with a liquid.

4. The gastric jejunal feeding device of claim 1, wherein the photoluminescent portion of the jejunal port is integrally coupled to the jejunal port or is externally positioned on the jejunal port.

5. The gastric jejunal feeding device of claim 1, wherein the photoluminescent portion of the jejunal port charges with minimal light exposure and lasts for 8 or more hours.

6. The gastric jejunal feeding device of claim 1, further comprising labels that are visible in the dark, wherein the labels are positioned on the photoluminescent portion of the jejunal port and include black ink or another different photoluminescent portion.

7. The gastric jejunal feeding device of claim 1, wherein:
   the gastric port has an opening with a notch for indicating orientation;
   the gastric port includes a blackened portion for indicating orientation; and
   the gastric connector includes a key for seating in the notch and allowing the gastric connector to be fully inserted into the gastric port.

\* \* \* \* \*